United States Patent [19]
Wacher et al.

[11] Patent Number: 5,962,522
[45] Date of Patent: Oct. 5, 1999

[54] PROPYL GALLATE TO INCREASE BIOAVAILABILITY OF ORALLY ADMINISTERED PHARMACEUTICAL COMPOUNDS

[75] Inventors: Vincent J. Wacher, San Francisco; Leslie Z. Benet, Belvedere, both of Calif.

[73] Assignee: AvMax, Inc., Berkeley, Calif.

[21] Appl. No.: 08/926,309

[22] Filed: Sep. 5, 1997

[51] Int. Cl.$^6$ .................................................. A61K 31/235
[52] U.S. Cl. ............................................................ 514/544
[58] Field of Search ............................................. 514/544

[56] References Cited

U.S. PATENT DOCUMENTS

| | | | |
|---|---|---|---|
| 4,310,543 | 1/1982 | Gallo-Torres | 424/305 |
| 5,156,842 | 10/1992 | Mulligan | 424/195.1 |
| 5,567,592 | 10/1996 | Benet et al. | 435/7.21 |
| 5,665,386 | 9/1997 | Benet et al. | 424/451 |

FOREIGN PATENT DOCUMENTS

| | | |
|---|---|---|
| 0 184 942 A2 | 6/1986 | European Pat. Off. . |
| 0 295 941 B1 | 12/1988 | European Pat. Off. . |
| 0 314 384 A2 | 5/1989 | European Pat. Off. . |
| 02202813 | 8/1990 | Japan . |
| 95/20980 | 8/1995 | WIPO . |

OTHER PUBLICATIONS

Bonkovsky et al., "Cytochrome $P_{450}$ of Small Intestinal Epithelial Cells," *Gastroenterology,* 88:458–467 (1985).

Bradford, M.M. "A rapid and sensitive method for the quantitation of microgram quantities of protein utilizing the principles of protein–dye binding." *Anal. Biochem.* 72:248–254 (1976).

Fabre, G., et al., Evidence of CYP3A–mediated N–deethylation of aminodarone in human liver microsomal fractions, *Drug Metabolism and Disposition,* 21(6):978–985 (1993).

Fasco et al., "Rat Small Intestinal Cytochromes P450 Probed by Warfarin Metabolism" *Mol. Pharmacol.,* 43:226–233 (1993).

Greenblatt, David J., "Presystemic Extraction: Mechanisms and Consequences," *J. Clin. Pharmcol.,* 33:650–656 (1993).

Gonzalez et al., Human P450PCN1: Sequence, Chromosome Localization, and Direct Evidence through cDNA Expression that P450PCN1 is Nifedipine Oxidase, *DNA,* 7(2):79–86 (1988).

Kaminsky et al., "Small Intestinal Cytochromes P450," *Toxicology,* 21(6):407–422 (1992).

Kivisto et al., "Plasma buspirone concentrations are greatly increased by erythromycin and itraconazole," *Clinical Pharmacology & Therapeutics,* 62(3):348–354 (1997).

Kolars, J.C. et al., "Identification of Rifampin–Inducible P450IIIA4 (CYP3A4) in Human Small Bowel Enterocytes," *J. Clin. Investig.,* 90:1871–1878 (1992).

Kolars et al., "Heterogeneity of Cytochrome P450IIIA Expression in Rat Gut Epithelia," *Gastroenterology,* 102:1188–1198 (1992).

Komori et al., "Cytochrome P–450 in Human Liver Microsomes: High–Performance Liquid Chromatographic Isolation of Three Forms and Their Characterization," *J. Biochem.,* 104:912–16 (1988).

Kronbach et al., "Cyclosporine Metabolism in Human Liver: Identification of a Cytochrome P–450III Gene Family as the Major Cyclosporine–Metabolizing Enzyme Explains Interactions of Cyclosprine with Other Drugs," *Clin. Pharmacol. Ther.,* 43(6):630–5 (1988).

Nash, "The Colorimetic Estimation of Formaldehyde by Means of the Hantzach Reaction," *Biochem. J.,* 55:416–421 (1953).

Schmiedlin–Ren et al., "Cultured Adult Rat Jejunal Explants as a Model for Studying Regulation of CYP3A," *Biochem. Pharmacol.,* 46(5):905–918 (1993).

Somberg et al., "The Clinical Implications of First–Pass Metabolism: Treatment Strategies for the 1990's," *J. Clin. Pharmcol.,* 33:670–673 (1993).

Tam, Yun K., "Individual Variation in First–Pass Metabolism," *Clin. Pharmacokinet,* 25(4):300–328 (1993).

Trivier et al., "Amiodarone N–deethylation in human liver microsomes: involvement of cytochrome P450 3A enzymes (first report)," *Life Sci.,* 52:PL91–96 (1993).

van Hoogdalem et al., "Intestinal Drug Absorbtion Enhancement: An Overview," *Pharmacol. Ther.,* 44:407–443 (1989).

Watkins et al., "Identification of Glucocorticoid–Inducible Cytochromes P–450 in the Intestinal Mucosa of Rats and Man," *J. Clin. Invest.,* vol. 80:1029–36 (1987).

Watkins et al., "The Role of Cytochromes P–450 in Cyclosporine Metabolism," *J. Am. Acad. Dermacol.,* 23:1301–1309 (1990).

Watkins et al., "Drug Metabolism by Cytochromes P450 in the Liver and Small Bowel," *Gastrointestinal Pharmacology,* 21(3):511–527 (1992).

WHO Food Additives Series, vol. 32:3–23 (1993), Abstract.

Wrighton et al., "Demonstration in Multiple Species of Inducible Hepatic Cytochromes P–450 and their mRNAs Related to the Glucocorticoid–Inducible Cytochrome P–450 of the Rat," *Molecular Pharmacology,* 28:312–321 (1985).

Wrighton et al., "Studies on the Expression and Metabolic Capabilities of Human Liver Cytochrome P450IIIA5 (HLp3)," *Molec. Pharmacol.,* 38:207–213 (1990).

Wu et al., "Use of IV and Oral Drug Levels from Cyclosporine (CsA) with Concomitant Rifampin to Differentiate Gut Absorption and Metabolism," *Pharm. Res.* 10 (1993) Abstract # PPDM 8185, (List continued on next page.)

*Primary Examiner*—Phyllis G. Spivack
*Attorney, Agent, or Firm*—Cooley Godward LLP

[57] ABSTRACT

A method for increasing bioavailability of an orally administered pharmaceutical compound comprises orally administering the pharmaceutical compound to a mammal in need of treatment with the compound concurrently with propyl gallate. Improved formulations of pharmaceutical compounds include propyl gallate to enhance the bioavailability of the active ingredient of the pharmaceutical compound.

23 Claims, No Drawings

OTHER PUBLICATIONS

Yang et al., "Inhibition of Hepatic Mixed Function Oxidase Activity by Propyl Gallate," *Biochemical Pharmacology*, 23:3129–3138 (1974).

Kelleher, J., et al., Modification of Paracetamol Hepatotoxicity by Anti–Oxidants, *J. Ind. Med. Res.*, 4 suppl. (4):138–144 (1976).

Kelleher, J., et al., Modification of Paracetamol Toxicity by Antioxidants, *Biochem. Soc. Transact.*, 4:292–294 (1976).

Kedderis, G. L., et al., "N–Demethylation Reactions Catalyzed by Chloroperoxides," *J. Biol. Chem.*, 255(21):10174–82 (1980).

Kedderis, G. L., et al., "Characterization of the N–Demethylation Reactions Catalyzed by Chloroperoxidase," *Microsomes, Drug Oxid., Chem. Carcinog.*, Int. Symp. Microsomes Drug Oxid., 1:351–4, pub. Academic Press, eds. Coon, et al. (1980).

Bamforth, K. J., et al., "*Common Food Additives are Potent Inhibitors of Humal Liver 17α–Ethinyloestradiol and Dopamine Sulphotransferases,*" *Biochemical Pharmacology*, 46(10):1713–1720 (1993).

Weinke, S., et al., "*Effect of Four Synthetic Antioxidants on the Formation of Ethylene from Methional in Rat Liver Microsomes,*" *Toxicology Letters*, 35:247–251 (1987).

PROPYL GALLATE TO INCREASE BIOAVAILABILITY OF ORALLY ADMINISTERED PHARMACEUTICAL COMPOUNDS

INTRODUCTION

1. Technical Field

This invention is directed to the field of pharmacology and particularly to the formulation of oral pharmaceutical compositions for increased bioavailability and reduced inter- and intra-individual variability.

2. Background

Pharmacokinetics is the study of the fate of pharmaceuticals from the time they are ingested until they are eliminated from the body. The sequence of events for an oral composition includes absorption through the various mucosal surfaces, distribution via the blood stream to various tissues, biotransformation in the liver and other tissues, action at the target site, and elimination of drug or metabolites in urine or bile.

Bioavailability of a drug (pharmaceutical composition) following oral dosing is a critical pharmacokinetic determinant which can be approximated by the following formula:

$$F_{oral} = F_{ABS} \times F_G \times F_H$$

where $F_{oral}$ is the oral bioavailability fraction, which is the fraction of the oral dose that reaches the circulation in an active, unchanged form. $F_{oral}$ is less than 100% of the active ingredient in the oral dose for four reasons: (1) drug is not absorbed out of the gut lumen into the cells of the intestine and is eliminated in the feces; (2) drug is absorbed into the cells of the intestine but back-transported into the gut lumen; (3) drug is biotransformed by the cells of the intestine (to an inactive metabolite); or (4) drug is eliminated by the cells of the liver, either by biotransformation and/or by transport into the bile. Thus, oral bioavailability is the product of the fraction of the oral dose that is absorbed ($F_{ABS}$), the fraction of the absorbed dose that successfully reaches the blood side of the gastrointestinal tract ($F_G$), and the fraction of the drug in the GI blood supply that reaches the heart side of the liver ($F_H$). The extent of gut wall absorption, back transport and metabolism, and liver elimination are all subject to wide inter- and intra-individual variability.

Previous investigations arising in the laboratory of one of the present inventors resulted in new understandings of factors involved with bioavailability and in the invention described in U.S. Pat. No. 5,567,592, issued Oct. 22, 1996. The '592 patent describes general methods for increasing bioavailability of oral pharmaceutical compositions and methods for identifying compounds that increase bioavailability. However, although that invention made it possible to investigate a number of classes of compounds not previously thought to be useful in enhancing bioavailability, the actual process of identifying specific classes of compounds that are superior bioenhancers, among those bioenhancers which work to some degree, still remains a process of investigation and discovery. Within many classes of substances identified as showing general bioenhancing effects, there is surprising variance from class member to class member in the extent of each compound's bioenhancing effect, and some compounds that would at first thought appear to be enhancers of drug bioavailability because of their membership in a generally effective class of compounds, actually are found to be agents that interfere with the bioavailability of drugs, although the mechanism by which such interference takes place is not yet known. In some cases, a single compound or small group of compounds has been found to be particularly potent as a bioenhancer despite resembling in structure other compounds that have less activity or that even reduce bioavailability.

Accordingly, it is important to identify and confirm the identity of individual compounds or classes of compounds that are particularly useful for enhancing bioavailability. For example, U.S. Pat. No. 5,665,386, issued on Sep. 9, 1997, discloses the use of essential oils to enhance bioavailability.

SUMMARY OF THE INVENTION

An object of this invention is to identify compositions with superior ability to increase drug bioavailability, particularly by increasing net drug absorption and/or decreasing drug biotransformation in the gut wall by inhibiting cytochrome P450 drug metabolism.

Another object of the invention is to provide compositions that strongly inhibit enzymes of the cytochrome P450 3A class (CYP3A) in the gut in preference to in other locations, such as the liver, which was previously thought to be the primary site of drug metabolism.

One specific object of the present invention is to reduce inter-individual variability of the systemic concentrations of the active pharmaceutical compound, as well as intra-individual variability of the systemic concentrations of the pharmaceutical compound being administered.

The invention is carried out by co-administering propyl gallate with an oral pharmaceutical compound (drug) or compounds to increase drug bioavailability. The compositions and methods of the invention can be used to increase drug efficacy in humans and in other mammals. Although veterinary use is specifically contemplated, the primary use will be in human treatment. Administration schemes include, but are not limited to, use of oral and topical formulations in humans and use of similar formulations for livestock.

DESCRIPTION OF SPECIFIC EMBODIMENTS

Propyl Gallate Increases Drug Bioavailability

The present invention arises from continued research into the factors affecting drug bioavailability that were described in earlier applications arising from the laboratory of one of the present inventors. "Drug bioavailability" is defined here as the total amount of drug systemically available over time. The present invention increases drug bioavailability by inhibiting drug biotransformation in the gut. The compound responsible for increased drug bioavailability is propyl gallate. It has been discovered that propyl gallate is capable of inhibiting the appropriate enzyme.

In general, the present invention provides a method for increasing the bioavailability of an orally administered pharmaceutical compound (particularly one which is hydrophobic) by orally administering the pharmaceutical compound to a mammal in need of treatment concurrently with propyl gallate in sufficient amount to provide integrated systemic concentrations over time of the compound greater than the integrated systemic concentrations over time of the compound in the absence of the propyl gallate. Changes in the integrated systemic concentrations over time are indicated by "area under the curve" (AUC) measurements, an accepted pharmacological technique described in detail below.

Propyl Gallate

The structure of propyl gallate (3,4,5-trihydroxybenzoic acid, n-propyl ester) is shown below:

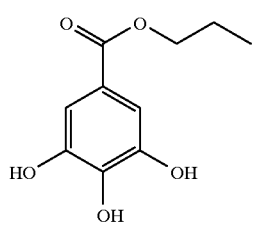

Propyl gallate has been used as an antioxidant or preservative in foods, drugs, cosmetics and pesticide products since 1948. This compound is Generally Recognized As Safe (GRAS) by the FDA and is listed in the Everything Added to Food in the United States (EAFUS) database as well as the United States Pharmacopeia-National Formulary (USP-NF) and the Food Chemicals Codex. The Joint Food and Agricultural Organization/World Health Organization Expert Committee on Food Additives has established an acceptable daily intake of 0–1.4 mg/kg/day for this compound. This value is 1/100 of the "no observed effect" level determined in a 90 day feeding study in rats ("Gallates: Propyl, Octyl, Dodecyl", WHO Food Additive Series, 32:3–23 (1993)).

The propyl gallate is preferably presented for coadministration in a propyl gallate to drug ratio in the range of 0.01 to 100 units propyl gallate to 1 unit of the drug. For example, a formulation having 1 mg propyl gallate per 100 mg drug represents the lower end of this range and a formulation having 500 mg propyl gallate per 5 mg drug represents the upper end of this range. A more preferred range of propyl gallate to drug in accordance with the present invention is 0.1 to 10 units propyl gallate to 1 unit of the drug. The most preferred range is 0.5 to 2 units propyl gallate per 1 unit of the drug. Because propyl gallate in very low concentrations, as has been used previously for the antioxidant purposes discussed above, is of low activity and thus not likely to be useful for the purposes described generally herein, only concentrations of propyl gallate providing an inhibition activity are included in the invention. Preferred are those formulations of propyl gallate that show an inhibition of at least 20% at a 1:1 propyl gallate:drug ratio; even more preferred are formulations of propyl gallate that show an inhibition of at least 50% at the same propyl gallate to drug ratio.

Bioavailability Measurements

The increase in drug bioavailability attributable to administration of the propyl gallate can be determined by measuring total systemic drug concentrations over time after coadministration of a drug and the propyl gallate and after administration of only the drug. The increase in drug bioavailability is defined as an increase in the Area Under the Curve (AUC). AUC is the integrated measure of systemic drug concentrations over time in units of mass-time/volume. The AUC from time zero (the time of dosing) to time infinity (when no drug remains in the body) following the administration of a drug dose is a measure of the exposure of the patient to the drug. When efficacy of the propyl gallate is being measured, the amount and form of active drug administered should be the same in both the coadministration of drug and propyl gallate and the administration of the drug alone. For instance, administration of 10 mg of drug alone may result in total systemic drug delivered over time (as measured by AUC) of 500 μg-hr/ml. In coadministration (i.e., in the presence of the propyl gallate) the systemic drug AUC may increase to 700 μg-hr/ml. If significantly increased drug bioavailability in the presence of the propyl gallate is anticipated, drug doses may need to be reduced for safety.

Systemic drug concentrations are measured using standard drug measurement techniques. "Systemic drug concentration" refers to a drug concentration in a mammal's bodily fluids, such as serum, plasma or blood; the term also includes drug concentrations in tissues bathed by the systemic fluids, including the skin. Systemic drug concentration does not refer to digestive fluids. The increase in total systemic drug concentrations is one way of defining an increase of drug bioavailability due to coadministration of propyl gallate and the drug. For drugs excreted in part unmetabolized in the urine, an increased amount of unchanged drug in the urine will reflect the increase in systemic concentrations.

Characteristics of Drugs Used With Propyl Gallate

The word "drug" as used herein is defined as a chemical capable of administration to an organism which modifies or alters the organism's physiology. More preferably the word "drug" as used herein is defined as any substance intended for use in the treatment or prevention of disease. Drug includes synthetic and naturally occurring toxins and bioaffecting substances as well as recognized pharmaceuticals, such as those listed in "The Physicians Desk Reference," 49th edition, 1995, pages 101–338; "Goodman and Gilman's The Pharmacological Basis of Therapeutics" 9th Edition (1996), pages 103–1645 and 1707–1792; and "The United States Pharmacopeia, The National Formulary", USP 23 NF 18 (1995), the compounds of these references being herein incorporated by reference. The term drug also includes compounds that have the indicated properties that are not yet discovered or available in the U.S. The term drug includes pro-active, activated and metabolized forms of drugs. The present invention can be used with drugs consisting of charged, uncharged, hydrophilic, zwitter-ionic, or hydrophobic species, as well as any combination of these physical characteristics. A hydrophobic drug is defined as a drug which in its non-ionized form is more soluble in lipid or fat than in water. A preferred class of hydrophobic drugs is those drugs more soluble in octanol than in water.

Compounds (or drugs) from a number of classes of compounds can be administered with propyl gallate, for example, but not limited to, the following classes: acetanilides, anilides, aminoquinolines, benzhydryl compounds, benzodiazepines, benzofurans, cannabinoids, cyclic peptides, dibenzazepines, digitalis gylcosides, ergot alkaloids, flavonoids, imidazoles, quinolines, macrolides, naphthalenes, opiates (or morphinans), oxazines, oxazoles, phenylalkylamines, piperidines, polycyclic aromatic hydrocarbons, pyrrolidines, pyrrolidinones, stilbenes, sulfonylureas, sulfones, triazoles, tropanes, and vinca alkaloids.

Increased Drug Bioavailability by Inhibition of Cytochrome P450

Phase I Biotransformation

Inhibition of enterocyte cytochromes P450 participating in drug biotransformation is one objective of the present invention. The major enzymes involved in drug metabolism are present in the endoplasmic reticulum of many types of cells but are at the highest concentration in hepatocytes. Traditionally, enterocyte biotransformation was considered of minor importance in biotransformation compared to the liver. Many compounds inhibit cytochrome P450. These include, but are not limited to, ketoconazole, troleandomycin, gestodene, flavones such as quercetin and naringenin, erythromycin, ethynyl estradiol, and prednisolone. The primary goal of the invention is to use propyl gallate to inhibit drug cytochrome P450 biotransformation in the gut to increase drug bioavailability.

Types of Cytochromes and Tissue Location

The cytochromes P450 are members of a superfamily of hemoproteins. They represent the terminal oxidases of the mixed function oxidase system. The cytochrome P450 gene superfamily is composed of at least 207 genes that have been named based on their evolutionary relationships. For this nomenclature system, the sequences of all of the cytochrome P450 genes are compared, and those cytochromes P450 that share at least 40% identity are defined as a family (designated by CYP followed by a Roman or Arabic numeral, e.g. CYP3), further divided into subfamilies (designated by a capital letter, e.g. CYP3A), which are comprised of those forms that are at least 55% related by their deduced amino acid sequences. Finally, the gene for each individual form of cytochrome P450 is assigned an Arabic number (e.g. CYP3A4).

Three cytochrome P450 gene families (CYP1, CYP2 and CYP3) appear to be responsible for most drug metabolism. At least 15 cytochromes P450 have been characterized to varying degrees in the human liver. At concentrations of the substrates found under physiologic conditions, enzyme kinetics often favor a single form of cytochrome P450 as the primary catalyst of the metabolism of a particular drug or other enzyme substrate.

The CYP3 gene family encoding cytochromes P450 of type 3 is possibly the most important family in human drug metabolism. At least 5 forms of cytochrome P450 are found in the human 3A subfamily, and these forms are responsible for the metabolism of a large number of structurally diverse drugs. In non-induced individuals, 3A may constitute 20% of the P450 enzymes in the liver. In enterocytes, members of the 3A subfamily constitute greater than 70% of the cytochrome-containing enzymes. The first two human 3A subfamily members identified were 3A3 and 3A4. These two cytochromes P450 are so closely related that the majority of studies performed to date have not been able to distinguish their contributions, and thus they are often referred to as 3A3/4. Erythromycin N-demethylation, cyclosporine oxidation, nifedipine oxidation, midazolam hydroxylation, testosterone 6β-hydroxylation, and cortisol 6β-hydroxylation are all in vitro probes of 3A3/4 catalytic activity. The levels of 3A3/4 vary by as much as 60-fold between human liver microsomal samples; with the levels of 3A forms approaching 50% of the total cytochrome P450 present in human liver samples from individuals receiving inducers of 3A3/4. The recently studied CYP3A5 may also play a role as important as 3A3/4.

The liver contains many isoforms of cytochrome P450 and can biotransform a large variety of substances. The enterocytes lining the lumen of the intestine also have significant cytochrome P450 activity, and this activity is dominated by a single family of isozymes, 3A, the most important isoforms in drug metabolism.

Increased Drug Efficacy By Reducing CYP3A Drug Biotransformation

Propyl gallate, as used according to the invention, reduces drug biotransformation in the gut by inhibiting CYP3A activity in gut epithelial cells which leads to a total increase in drug bioavailability in the serum. In the presence of propyl gallate, fewer drug molecules will be metabolized by phase I enzymes in the gut and will not be available for phase II conjugation enzymes. This will lead to increased concentrations of untransformed drug passing from the gut into the blood and onto other tissues in the body.

Although the primary objective of the propyl gallate is to inhibit CYP3A drug biotransformation in the gut, some biotransformation may be decreased in other tissues as well if the propyl gallate is absorbed into the blood stream. The decrease in biotransformation by other tissues will also increase drug bioavailability. The advantage of targeting propyl gallate to the gut, however, is that it allows the use of lower systemic concentrations of propyl gallate compared to inhibitors that target CYP3A in the liver. After oral administration of propyl gallate, concentrations will be highest at the luminal surface of the gut epithelia, not having been diluted by systemic fluids and the tissues of the body. Luminal concentrations that are greater compared to blood concentrations will permit preferential inhibition of CYP3A in gut instead of the liver. Propyl gallate preferentially inhibits gut CYP3A and so, will also be a particularly effective means of increasing drug bioavailability.

Coadministration of propyl gallate will also reduce variability of oral bioavailability. Reduction of drug biotransformation or increased drug absorption will decrease variability of oral bioavailability to some degree because the increase in bioavailability will begin to approach the theoretical maximum of 100% oral bioavailability. The increase in oral bioavailability will be generally larger in subjects with lower oral bioavailability. The result is a reduction in inter-individual and intra-individual variation. Addition of propyl gallate will reduce inter-individual and intra-individual variation of systemic concentrations of a drug or compound.

A Net Increase in Drug Bioavailability Due to a Decrease in the Activity of CYP3A The catalytic activities of CYP3A that are subject to inhibition include, but are not limited to, dealkyase, oxidase, and hydrolase activities. In addition to the different catalytic activities of CYP3A, different forms of CYP3A exist with a range in molecular weight (for example, from 51 kD to 54 kD, as shown in Komori et al., *J. Biochem.*, 104:912–16 (1988)).

Propyl gallate reduces CYP3A drug biotransformation by acting as an inhibitor of CYP3A activity. Possible mechanisms include competitive, non-competitive, uncompetitive, mixed or irreversible inhibition of CYP3A drug biotransformation.

Selection of Propyl Gallate Concentration by Reduction of CYP3A Drug

Biotransformation

The ability of the propyl gallate to increase drug bioavailability of a particular drug can be estimated using in vitro and in vivo drug biotransformation measurements. In vivo measurements of drug bioavailability, such as measuring serum or blood drug concentrations over time, provide the closest measure of total drug systemic availability (bioavailability). In vitro assays of CYP3A metabolism indirectly indicate drug bioavailability because CYP3A drug metabolism affects integrated systemic drug concentrations over time. Although even a minimally measured increase is all that is required for propyl gallate to be useful, a preferred commercially desirable concentration of propyl gallate acting as a CYP3A modulator generally will increase drug bioavailability by at least 10%, preferably by at least 50%, and more preferably by at least 75% of the difference between bioavailability in its absence and complete oral bioavailability. For example, if the drug bioavailability is 40% without propyl gallate, then the addition of propyl gallate may increase bioavailability to 85%, for a 75% increase. A sufficient amount of orally administered propyl gallate will provide integrated systemic drug concentrations over time greater than the integrated systemic drug concentrations over time in the absence of propyl gallate. The actual amount or concentration of propyl gallate to be included with a pharmaceutical compound for a particular composition or formulation will vary with the active ingredient of the compound. The amount of the propyl gallate to be used should be optimized using the AUC methods described herein, once the components for a particular pharmaceutical composition have been decided upon. As stated above, the recommended measure for the amount of propyl gallate in a particular formulation is by direct comparison to the amount of drug, with a propyl gallate:drug ratio in the range of of 0.01–100:1 being preferred, 0.1–10:1 being more preferred, and 0.5–2:1 being most preferred.

Inhibition of the P450 3A class of enzymes by propyl gallate can be studied by a variety of bioassays, several of which are set forth below.

In vitro CYP3A Assays and Increased Drug Bioavailability

Cell Assays of CYP3A Function and Increased Drug Bioavailability

Cultured cells of either hepatocytes or enterocytes or freshly prepared cells from either liver or gut can be used to determine the activity of propyl gallate as a CYP3A inhibitor. Various methods of gut epithelial cell isolation can be used such as the method of Watkins et al., *J. Clin. Invest.*, 80:1029–36 (1985). Cultured cells, as described in Schmiedlin-Ren et al., *Biochem. Pharmacol.*, 46:905–918 (1993), can also be used. The production of CYP3A metabolites in cells can be measured using high pressure liquid chromatograph (HPLC) methods as described in the following section for microsome assays of CYP3A activity.

Microsome Assays of CYP3A Function and Increased Bioavailability

Microsomes from liver or intestine will be used for assays of CYP3A activity. Microsomes can be prepared from liver using conventional methods as discussed in Kronbach et al., *Clin. Pharmacol. Ther.*, 43:630–5 (1988). Alternatively, microsomes can be prepared from isolated enterocytes using the method of Watki et al., *J. Clin. Invest.*, 80:1029–1037 (1987). Microsomes from gut epithelial cells can also be prepared using calcium precipitation as described in Bonkovsky et al., *Gastroenterology*, 88:458–467 (1985). Microsomes can be incubated with drugs and the metabolites monitored as a function of time. In addition, the levels of these enzymes in tissue samples can be measured using radioimmunoassays or western blots. Additionally, the production of metabolites can be monitored using high pressure liquid chromatography systems (HPLC) and identified based on retention times. CYP3A activity can also be assayed calorimetrically measuring erythromycin demethylase activity as the production of formaldehyde as in Wrighton et al., *Mol. Pharmacol.*, 28:312–321 (1985) and Nash, *Biochem. J.*, 55:416–421 (1953).

Characteristics of Propyl Gallate for Reducing CYP3A Drug Metabolism

Propyl gallate binds CYP3A quickly and inhibits while the drug is passing through the enterocyte. After the propyl gallate reaches the heart and is distributed throughout the body the concentration of the propyl gallate will be diluted on future passes through the liver. Concentrations of propyl gallate used in the gut lumen are preferably selected to be effective on gut CYP3A metabolism but, due to dilution, to be less active in other tissues.

The amount of propyl gallate used for oral administration can be selected to achieve small intestine luminal concentrations of at least 0.1 of the $K_i$ or apparent $K_i$ for CYP3A inhibition of drug metabolism or an amount sufficient to increase systemic drug concentration levels, whichever is less. Alternatively, the amount of an inhibitor of cytochrome P450 3A enzyme that will be used in a formulation can be calculated by various assays that are described in detail below. For example, one such assay measures the conversion of nifedipine to its oxidation product in an assay system containing 500 $\mu$g human liver microsomes, 25 $\mu$M nifedipine, and 1 mm NADPH in 500 $\mu$l of 0.1 M sodium phosphate buffer, pH 7.4. The initial inhibitor amount is selected to provide concentrations in the lumen of the small intestine equal or greater than concentrations that reduce the rate of conversion determined by this assay, preferably a rate reduction of at least 10%. While the actual dose of inhibitor in a clinical formulation might be optimized from this initial dosage depending on the results of a clinical trial, the assay as described is sufficient to establish a utilitarian dosage level.

In all of these cases, the goal of selecting a particular concentration is increased bioavailability of the pharmaceutical compound that is being administered. Thus, a desirable goal is to provide integrated systemic concentrations over time of the pharmaceutical compound in the presence of the inhibitor that is greater than the integrated systemic concentrations over time of the pharmaceutical compound in the absence of the inhibitor by at least 10% of the difference between bioavailability in its absence and complete oral bioavailability. Preferred is attaining of "complete bioavailability," which is 100% systemic bioavailability of the administered dosage.

Screening Assay for Superior Propyl Gallate Formulations

In summary, the various techniques described above for screening propyl gallate concentrations for activity levels by assaying for inhibition in the gut of a mammal of activity of a cytochrome P450 enzyme are all generally useful as methods of creating useful formulations that are most useful for increasing bioavailability of the active ingredient of a given drug in a mammal. In all of these assays, the best amounts are those that best inhibit enzymatic destruction of a tested drug in the gut of the mammal (either by direct testing in vivo or by a test that predicts such activity). When testing for inhibition of activity of a cytochrome enzyme, assays that detect inhibition of members of a cytochrome P450 3A family (for a particular mammal, particularly human) are preferred. Although in vivo assays are preferred, because of the direct relationship between the measurement and gut activity, other assays, such as assays for inhibition of cytochrome P450 activity in isolated enterocytes or hepatocytes or microsomes obtained from either enterocytes or hepatocytes of the mammal in question or for inhibition of cytochrome P450 in a tissue or membrane from the gut of said mammal, are still useful as screening assays. It is possible to use enzymes from both the gut and liver interchangeably for these assays since it has been shown that CYP3A enzymes are identical in the two locations (Kolars, J. C. et al., Identification of Rifampin-Inducible P450III A4 (CYP3A4) in Human Small Bowel Enterocytes, *J. Clin. Investig.*, 90:1871–1878 (1992)).

Coadministration and Delivery of the Propyl Gallate

Coadministration of Propyl Gallate and a Drug

The present invention will increase the bioavailability of a drug in systemic fluids or tissues by co-administering the propyl gallate with a drug. "Co-administration" includes concurrent administration (administration of the propyl gallate and drug at the same time) and time-varied administration (administration of the propyl gallate at a time different from that of the drug), as long as both the propyl gallate and the drug are present in the gut lumen and/or membranes during at least partially overlapping times. "Systemic fluids or tissues" refers to blood, plasma, or serum and to other body fluids or tissues in which drug measurements can be obtained.

Delivery Vehicles and Methods

Coadministration can occur with the same delivery vehicle or with different delivery vehicles. The propyl gallate and the drug can be administered using, as examples, but not limited to, time release matrices, time release coatings, companion ions, and successive oral administrations. Alternatively, the drug and the propyl gallate can be separately formulated with different coatings possessing different time constants for release of propyl gallate and drug. Propyl gallate can also be bound to the drug being protected, either by covalent bonding or by ionic or polar attractions.

Propyl gallate also increase bioavailability when used with epithelia tissues other than the gut. The discussion above of the invention as used in the gut is appropriate for other types of epithelia. For example, CYP 3A enzymes are present in the skin, and propyl gallate can be used in transdermal formulations to increase drug bioavailability to systemic fluids and tissues. Such applications are part of the invention, since inhibition of CYP 3A enzymes by propyl gallate in epithelia other than the gut provides the same mechanism of action.

Formulations Having Propyl Gallate

The invention is carried out in part by formulating an oral pharmaceutical composition to contain propyl gallate. This is accomplished in some embodiments by admixing a pharmaceutical compound, usually a pharmaceutical carrier, and propyl gallate, the propyl gallate being present in an amount sufficient to provide integrated systemic concentrations over time of the compound (as measured by AUC's greater than the integrated systemic concentrations over time of the compound in the absence of the composition) when the pharmaceutical composition is administered orally to an animal being treated. A pharmaceutical carrier is generally an inert bulk agent added to make the active ingredients easier to handle and can be solid or liquid in the usual manner as is well understood in the art. Pharmaceutical compositions produced by the process described herein are also part of the present invention.

The present invention can also be used to increase the bioavailability of the active compound of an existing oral pharmaceutical composition. When practiced in this manner, the invention is carried out by reformulating the existing composition to provide a reformulated composition by admixing the active compound with propyl gallate, the propyl gallate being present in an amount sufficient to provide integrated systemic concentrations over time of the compound when administered in the reformulated composition greater than the integrated systemic concentrations over time of the compound when administered in the existing pharmaceutical composition. All of the criteria described for new formulations also apply to reformulation of old compositions. In preferred aspects of reformulations, the reformulated composition comprises all components present in the existing pharmaceutical composition plus the propyl gallate, thus simplifying practice of the invention, although it is also possible to eliminate existing components of formulations because of the increase in bioavailability. Thus, the invention also covers reformulated compositions that contain less than all components present in the existing pharmaceutical composition plus the propyl gallate. However, this invention does not cover already existing compositions that contain a component which increases bioavailability by mechanisms described in this specification (without knowledge of the mechanisms), should such compositions exist.

Traditional formulations can be used with propyl gallate. Optimal propyl gallate concentrations can be determined by varying the amount and timing of propyl gallate administration and monitoring bioavailability. Once the optimal propyl gallate concentration or propyl gallate to drug ratio is established for a particular drug, the formulation (propyl gallate, drug, and other formulation components, if any) is tested clinically to verify the increased bioavailability. In the case of time- or sustained-release formulations, it will be preferred to establish the optimal propyl gallate concentration using such formulations from the start of the bioavailability experiments.

Propyl gallate has been used as an antioxidant under many different circumstances, including as part of a pharmaceutical composition or formulation. Its use has been limited to preventing decomposition of the materials in the formulation, rather than for a physiological effect. As an antioxidant, propyl gallate is used in small quantities, and such materials are not likely to approach even the outer limits of the present invention as defined by the specification and claims. In particular, preferred formulations of the invention contain at least 1% by weight propyl gallate relative to the total weight of the formulation (including the capsule, if present), more preferably at least 2%, even more preferably at least 5%. In most cases propyl gallate used as an antioxidant is used at less than 0.1% of the materials they are being used to protect or preserve. In considering these percentages, it should be recalled that these are percentages of the formulation in which the active ingredient is being presented, not percentages by weight or volume as concentrations in the medium in which the pharmaceutical composition will become dissolved or suspended after ingestion of the formulation. Furthermore, propyl gallate may be used in capsules (either hard or soft standard pharmaceutical gel capsules, for example).

The invention now being generally described, the same will be better understood by reference to the following detailed example, which is offered for illustration only and is not to be considered limiting of the invention unless otherwise specified.

EXAMPLE

Inhibition of Drug Degradation by Propyl Gallate

The ability of propyl gallate at various concentrations to inhibit metabolism for three representative drugs through inhibition of the cytochrome P450 mechanism was tested. Human liver microsomes were prepared and each of three drugs, amiodarone, buspirone, or nifedipine, were incubated with the microsomes in the presence of propyl gallate or a known inhibitor of CYP3A metabolism. Metabolism in the presence of propyl gallate or known CYP3A inhibitor was compared to a control treated only with the vehicle in which the inhibitor was dissolved.

Inhibition of metabolism of the known CYP3A substrates amiodarone (Fabre, G., et al., Evidence for CYP3A-mediated N-deethylation of amiodarone in human liver microsomal fractions, *Drug Metab. Dispos.*, 21:978–985 (1993), Triver, J. M., et al., Amiodarone N-deethylation in human liver microsomes: involvement of cytochrome P450 3A enzymes (first report), *Life Sci.*, 52:PL91–96 (1993)), nifedipine (Gonzalez, F. J., et al., Human P450PCN1: sequence, chromosome localization, and direct evidence through cDNA expression that P450PCN1 is nifedipine oxidase, *DNA*, 2:79–86 (1988)), and buspirone (Wacher, V. J., et al., Buspirone is metabolized by CYP3A but is not transported by P-glycoprotein. Pharm. Res. submitted) by human liver microsomes was tested.

To prepare the microsomes, human liver pieces were perfused with 1.15% potassium chloride then homogenized in 0.1 mM Tris-acetate, pH 7.4, containing 1 mM EDTA and 20 mM BHT. Microsomal pellets were prepared from the homogenate using standard differential centrifugation procedures (Guengerich, Analysis and characterization of enzymes in *Principles and Methods of Toxicology*, A. W. Hayes (ed.), Raven Press, New York. pp. 777–814 (1989)) and were stored at −80° C. in Tris-acetate buffer, pH 7.4, containing 20% w/v glycerol. Microsomes were diluted in 100 mM potassium phosphate buffer, pH 7.4, for use in metabolic incubations. Microsomal protein and CYP content of the human liver microsomes were determined using methods of Bradford (Bradford, M. M. A rapid and sensitive method for the quantitation of microgram quantities of protein utilizing the principles of protein-dye binding. *Anal. Biochem.* 72:248–254 (1976)) and Omura and Sato (Omura, T. et. al. The carbon monoxide-binding pigment of liver microsomes II. Solubilization, purification and properties. *J. Biol. Chem.* 239:2370–2378 (1964)), respectively.

The amiodarone was present in a concentration of 100 $\mu$M, the buspirone was in a concentration of 25 $\mu$M, and the nifedipine was present in a concentration of 25 $\mu$M. The propyl gallate was tested with each of these drugs at concentrations of 25, 50, and 100 $\mu$M. Other inhibitors of CYP3A metabolism were utilized at known inhibition concentrations, i.e. ketoconazole at 1 $\mu$M, cyclosporine at 25 $\mu$M, and diltiazem, erythromycin, and verapamil at 100 $\mu$M.

The drug and optionally the inhibitor were preincubated with the microsomes at 1 nmol CYP/ml and 1 mM diethylenetriaminepentaacetic acid (DETAPAC) in 100 mM phosphate buffer, pH 7.4 for 5 minutes at 37° C. After the preincubation, metabolic reactions were started by the addition of 1 mM reduced nicotinamide adenine dinucleotide phosphate (NADPH). Samples were taken at 1, 2, and 3 minutes after the start of the reaction and analyzed by High Performance Liquid Chromatography (HPLC). Disappearance of substrate and/or formation of metabolite were quantitated by comparison to standard curves.

The results are presented in Table 1 below. The metabolism rates (nmol/ml/min) are the mean±standard deviation of three measurements. Also shown in Table 1 are the metabolism rates expressed as a percentage of the control for each drug. These numbers are presented in parentheses.

TABLE 1

Inhibition of CYP3A-Mediated Metabolism in Human Liver Microsomes by Propyl Gallate

| Inhibitor | $\mu$M | Amiodarone[a] | Buspirone[b] | Nifedipine[c] |
|---|---|---|---|---|
| Control | | 1.92 ± 0.08 (100) | 5.37 ± 0.56 (100) | 4.36 ± 0.17 (100) |
| Propyl Gallate | 25 | 0.94 ± 0.02 (49) | 3.49 ± 0.49 (65) | 3.57 ± 0.29 (82) |
| | 50 | 0.55 ± 0.02 (28) | 2.25 ± 0.25 (42) | 2.35 ± 0.10 (54) |
| | 100 | 0.32 ± 0.03 (17) | 1.55 ± 0.23 (29) | 1.43 ± 0.04 (33) |
| Ketoconazole | 1 | 0.79 ± 0.004 (4) | 1.47 ± 0.39 (28) | 0.48 ± 0.06 (11) |
| Cyclosporine | 25 | 0.32 ± 0.03 (17) | 2.21 ± 0.38 (41) | 1.05 ± 0.02 (24) |
| Diltiazem | 100 | 1.06 ± 0.02 (55) | 2.80 ± 0.18 (52) | 3.74 ± 0.16 (86) |
| Erythromycin | 100 | 0.84 ± 0.07 (44) | 3.59 ± 0.46 (67) | 2.67 ± 0.11 (61) |
| Verapamil | 100 | 0.81 ± 0.04 (42) | 2.34 ± 0.46 (44) | 3.00 ± 0.05 (69) |

[a]Formation rate of N-desethylamiodarone metabolite (nmol/ml/min)
[b]Buspirone disappearance (nmol/ml/min)
[c]Formation of nifedipine oxidation product 2,6-dimethyl-4-(2-nitrophenyl)-3,5-pyridinedicarboxylic acid, dimethyl ester (nmol/ml/min)

As evidenced above, propyl gallate at all tested concentrations and against each drug, served as an effective inhibitor of CYP3A-mediated metabolism. Greater inhibition of the metabolism occurred with increasing concentrations of propyl gallate. Propyl gallate also compared favorably with the known CYP3A inhibitors tested. Specifically, propyl gallate was found to be better at inhibiting drug metabolism than the established CYP3A inhibitors diltiazem, erythromycin, and verapamil. This demonstrates the utility of propyl gallate to increase bioavailability of compounds by coadministration of propyl gallate with a pharmaceutical compound.

All publications and patent applications mentioned in this specification are herein incorporated by reference to the same extent as if each individual publication or patent application was specifically and individually indicated to be incorporated by reference. The invention now being fully described, it will be apparent to one of ordinary skill in the art that many changes and modifications can be made thereto without departing from the spirit or scope of the appended claims.

We claim:

1. A method for increasing bioavailability of an orally administered pharmaceutical compound, which comprises:

orally coadministering (1) the pharmaceutical compound to a mammal in need of treatment with the compound and (2) propyl gallate in an amount of the propyl gallate sufficient to provide bioavailability of the compound in the presence of the propyl gallate greater than bioavailability of the compound in the absence of the propyl gallate, the amount being at least 1% by weight relative to the total weight of a mixture including (1) and (2).

2. The method of claim 1, wherein the propyl gallate is coadministered in a range of 0.01 to 100 units propyl gallate per 1 unit of the pharmaceutical compound.

3. The method of claim 2, wherein the propyl gallate is coadministered in a range of 0.1 to 10 units propyl gallate per 1 unit of the pharmaceutical compound.

4. The method of claim 3, wherein the propyl gallate is coadministered in a range of 0.5 to 2 units propyl gallate per 1 unit of the pharmaceutical compound.

5. The method of claim 1, wherein the pharmaceutical compound is hydrophobic.

6. The method of claim 1, wherein the amount is sufficient to produce a concentration of the propyl gallate in the lumen of the gut of the mammal of at least 0.1 times a $K_i$ or apparent $K_i$ of CYP3A inhibition of the compound.

7. The method of claim 1, wherein bioavailability of the compound in the presence of the propyl gallate is greater than bioavailability of the compound in the absence of the propyl gallate by at least 10% of the difference between bioavailability in the absence of the propyl gallate and complete oral bioavailability.

8. The method of claim 7, wherein bioavailability of the compound in the presence of the propyl gallate is greater than bioavailability of the compound in the absence of the propyl gallate by at least 50% of the difference between bioavailability in the absence of the propyl gallate and complete oral bioavailability.

9. The method of claim 8, wherein bioavailability of the compound in the presence of the propyl gallate is greater than bioavailability of the compound in the absence of the propyl gallate by at least 75% of the difference between bioavailability in the absence of the propyl gallate and complete oral bioavailability.

10. The method of claim 1, wherein the propyl gallate shows an inhibition of at least 20% when the propyl gallate and the compound are present in a 1:1 propyl gallate:compound ratio.

11. The method of claim 1, wherein the pharmaceutical compound comprises an acetanilide, aminoacridine, aminoquinoline, anilide, anthracycline antibiotic, antiestrogen, benzazepine, benzhydryl compound, benzodiazapine, benzofuran, cannabinoid, cephalosporine, colchicine, cyclic peptide, dibenzazepine, digitalis glycoside, dihydropyridine, epiphodophyllotoxin, ergeline, ergot alkaloid, imidazole, isoquinoline, macrolide, naphthalene, nitrogen mustard, opioid, oxazine, oxazole, phenothiazine, phenylalkylamine, phenylpiperidine, piperazine, piperidine, polycyclic aromatic hydrocarbon, pyridine, pyridone, pyrimidine, pyrrolidine, pyrrolidinone, quinazoline, quinoline, quinone, rauwolfia alkaloid, retinoid, salicylate, steroid, stilbene, sulfone, sulfonylurea, taxol, triazole, tropane, or vinca alkaloid.

12. The method of claim 1, wherein the propyl gallate is present as a counter ion of the pharmaceutical compound.

13. The method of claim 1 wherein the propyl gallate is covalently bound to the pharmaceutical compound.

14. A method of formulating an oral pharmaceutical composition, which comprises:

admixing a pharmaceutical compound, a pharmaceutical carrier, and propyl gallate, the propyl gallate being present in sufficient amount to provide bioavailability of the pharmaceutical compound in the presence of the propyl gallate greater than the bioavailability of the pharmaceutical compound in the absence of the propyl gallate when the pharmaceutical composition is administered orally to a mammal, wherein the propyl gallate is present in an amount sufficient to provide at least 1% by weight propyl gallate relative to the total weight of the pharmaceutical composition.

15. The method of claim 14, wherein the propyl gallate is present in an amount sufficient to produce a concentration of the propyl gallate in the lumen of the gut of the mammal of at least 0.1 times a $K_i$ or apparent $K_i$ of CYP3A inhibition of the compound.

16. The method of claim 14, wherein the propyl gallate is present as a ion of the pharmaceutical compound.

17. The method of claim 14, wherein the propyl gallate is covalently bound to the pharmaceutical compound.

18. The method of claim 14, wherein the pharmaceutical compound comprises an acetanilide, aminoacridine, aminoquinoline, anilide, anthracycline antibiotic, antiestrogen, benzazepine, benzhydryl compound, benzodiazapine, benzofuran, cannabinoid, cephalosporine, colchicine, cyclic peptide, dibenzazepine, digitalis glycoside, dihydropyridine, epiphodophyllotoxin, ergeline, ergot alkaloid, imidazole, isoquinoline, macrolide, naphthalene, nitrogen mustard, opioid, oxazine, oxazole, phenothiazine, phsnylalkylamine, phenylpiperidine, piperazine, piperidine. polycyclic aromatic hydrocarbon, pyridine, pyridone, pyrimidine, pyrrolidine, pyrrolidinone, quinazoline, quinoline, quinone, rauwolfia alkaloid, retinoid, salicylate, steroid, stilbene, sulfone, sulfonylurea, taxol, triazole, tropane, or vinca alkaloid.

19. A pharmaceutical composition produced by the process of claim 14.

20. A method of increasing bioavailability of the active compound of an existing oral pharmaceutical composition, which comprises: reformulating the existing composition to provide a reformulated oral composition by admixing the active compound with propyl gallate, the propyl gallate being present in sufficient amount to provide bioavailability of the active compound when administered in the reformulated composition greater than said bioavailability of the active compound when administered in the existing pharmaceutical composition, wherein the propyl gallate is present is an amount sufficient to provide at least 1% by weight propyl gallate relative to the total weight of the reformulated oral composition.

21. The method of claim 20, wherein the reformulated oral compositioin comprises all components present in the existing pharmaceutical composition plus the propyl gallate.

22. The method of claim 20, wherein the reformulated oral composition contains less than all components present in the existing pharmaceutical composition plus the propyl gallate.

23. A reformulated oral pharmaceutical composition produced by the process of claim 20.

* * * * *

UNITED STATES PATENT AND TRADEMARK OFFICE
CERTIFICATE OF CORRECTION

PATENT NO. : 5,962,522  
DATED : October 5, 1999  
INVENTOR(S) : Vincent J. Wacher, et al.

Page 1 of 1

It is certified that error appears in the above-identified patent and that said Letters Patent is hereby corrected as shown below:

Column 13, claim 11,
Line 67, replace "taxol" with -- paclitaxel --.

Column 14, claim 18,
Line 42, replace "taxol" with -- paclitaxel --.

Signed and Sealed this

Twenty-first Day of August, 2001

*Attest:*

NICHOLAS P. GODICI
*Acting Director of the United States Patent and Trademark Office*

*Attesting Officer*